United States Patent
Dageforde

(10) Patent No.: US 6,497,156 B2
(45) Date of Patent: Dec. 24, 2002

(54) METHOD FOR COLLECTING EXHAUST GASES

(75) Inventor: Allen F. Dageforde, Orange, CA (US)

(73) Assignee: Horiba Instruments, Inc., Irving, CA (US)

( * ) Notice: Subject to any disclaimer, the term of this patent is extended or adjusted under 35 U.S.C. 154(b) by 0 days.

(21) Appl. No.: 10/189,668

(22) Filed: Jul. 3, 2002

(65) Prior Publication Data

US 2002/0166393 A1 Nov. 14, 2002

Related U.S. Application Data

(62) Division of application No. 09/473,280, filed on Dec. 28, 1999.

(51) Int. Cl.⁷ .................................................. G01N 1/00
(52) U.S. Cl. ................................ 73/863.23; 73/864.51; 73/864.62; 95/45
(58) Field of Search .......................... 95/45, 43, 47–56; 73/23.31, 863.03, 864.62, 863.23, 863, 864, 864.51; 239/6; 383/38, 40, 904, 902; 55/361, 364, 369, 370, 371, 380; 422/101, 102, 239, 177, 168, 238; 435/297.1; 604/410; 210/348; 96/7; 128/914, 205.12

(56) References Cited

U.S. PATENT DOCUMENTS

| | | | |
|---|---|---|---|
| 2,327,225 A | | 8/1943 | Taylor |
| 3,461,727 A | * | 8/1969 | Everhard et al. |
| 3,596,441 A | | 8/1971 | Lundahl |
| 3,867,923 A | | 2/1975 | West |
| 4,004,882 A | | 1/1977 | Byrne et al. |
| 4,061,467 A | | 12/1977 | Becker et al. |
| 4,132,594 A | | 1/1979 | Bank et al. |
| 4,188,989 A | | 2/1980 | Andersen |
| 4,874,586 A | | 10/1989 | Szymanski et al. |
| 5,071,760 A | | 12/1991 | Watanabe et al. |
| 5,077,036 A | | 12/1991 | Long, Jr. |
| 5,174,163 A | | 12/1992 | Gussman et al. |
| 5,178,021 A | | 1/1993 | Kosuth |
| 5,333,903 A | * | 8/1994 | Eyrainer et al. |
| 5,334,239 A | | 8/1994 | Choe et al. |
| 5,417,855 A | | 5/1995 | Gershenson |
| 5,650,565 A | | 7/1997 | Nagy et al. |
| 6,082,585 A | | 7/2000 | Mader et al. |
| 6,162,396 A | | 12/2000 | Bitensky et al. |

* cited by examiner

Primary Examiner—Joseph W. Drodge
Assistant Examiner—Terry K. Cecil
(74) Attorney, Agent, or Firm—Brooks & Kushman P.C.

(57) ABSTRACT

A sample of gaseous constituents, to be used in e.g. emissions testing, is collected within an inner bag 86 having a wall 92 that allows limited diffusion of at least one of the gaseous constituents therethrough. A control gas is then collected into an outer bag 82 that defines an auxiliary chamber 94 between the wall and the outside environment. The control gas controls the rate of diffusion of the at least one constituent through the wall and into the outside environment.

4 Claims, 2 Drawing Sheets

METHOD FOR COLLECTING EXHAUST GASES

CROSS-REFERENCE TO RELATED APPLICATIONS

This application is a divisional of copending application Ser. No. 09/473,280 filed on Dec. 28, 1999.

TECHNICAL FIELD

The present invention relates to sampling techniques for analysis of gaseous constituents in which a gas sample is collected in a sample bag.

BACKGROUND ART

A gas diluting and testing apparatus is used to analyze, among other things, vehicular exhaust. The apparatus uses a mixing tee to dilute the exhaust gasses so that the moisture content of the gasses is sufficiently reduced in order to minimize errors due to condensation. Existing mixing tees have a dilution inlet for receiving a dilution gas, a gaseous inlet for receiving the exhaust gasses, and a mixing portion where the gasses are brought together to form a diluted exhaust gas mixture.

In some systems, a sample of the diluted exhaust gas mixture is routed directly to external equipment, such as an analysis unit. Many times, a sample of the dilution gas is also sent directly to an analysis unit so that the subsequent analysis can more accurately determine what content is due to the exhaust gasses and what content is due to the dilution gas.

Because the hydrocarbon content of vehicle emissions is becoming smaller and smaller due to advances in technology, sometimes motivated by strict emission requirements, extra special care must be taken to assure that the diluted exhaust gas mixture is analyzed properly. Many factors that at one time presented negligible errors in the analysis of hydrocarbon (and other) constituent content in vehicular emissions are now significant because the constituent concentration is at such a low level, but must be measured with accuracy and precision. Of course, the problem of additional factors contributing to measurement error when the constituent to be measured has an exceedingly small concentration is not only present in the field of vehicle emission testing, the problem may also be present in other areas where gasses are analyzed to determine constituent content where the constituents of interest have very small concentrations.

As mentioned above, some approaches for measuring and analyzing gaseous constituent content in a test gas mixture use a mixing tee to dilute the gas mixture (for example, vehicle exhaust) by adding a dilution gas to the test gasses, producing a resultant mixture of test gasses and the dilution gas. The resultant mixture is then analyzed. In addition, the dilution gas may be analyzed so that content in the resultant mixture due to the test gasses can be distinguished from content in the resultant mixture due to the dilution gas. Some other measurement techniques use a different approach. In a different approach, the gasses, instead of being sent directly to an analysis unit, are collected in sample bags. Gasses are only kept in the sample bags for a short period of time, before the sample bags are connected to an analyzer. A gas collecting system that collects gasses in sample bags still faces the same problem of additional factors contributing to measurement error.

One existing system that uses sample bags to collect gas samples uses a sample bag made of polyvinylfloride (PVF) resin. The PVF sample bag has been used for many applications that have been commercially successful. However, the manufacturing process used to manufacture the PVF sample bag results in a small amount of hydrocarbons mixed in the PVF sample bag walls. When a gas sample (dilution gas or gas mixture such as exhaust gasses and dilution gas) is collected in the sample bag, hydrocarbons from the bag may slightly contaminate the gas sample. In many applications, the amount of hydrocarbon content contributed by the PVF sample bag to the gas sample is negligible when compared to the hydrocarbon content of the gas in the sample bag. As such, in many applications for exhaust gas analysis in which hydrocarbon content is to be measured, the PVF sample bags are suitable. However, as the hydrocarbon content within the gas sample becomes increasingly smaller, due in part to strict emission requirements for vehicles, the contribution of hydrocarbons to the gas sample from the PVF sample bag becomes a significant source of measurement error.

For the foregoing reasons, there is a need for an improved gas sample bag that reduces hydrocarbon contribution to the gas sample from the sample bag, without introducing other significant errors so that the overall integrity of the sample is increased.

DISCLOSURE OF INVENTION

It is, therefore, an object of the present invention to provide a sample bag for collecting a sample of gaseous constituents in which the sample chamber wall allows limited but significant diffusion of a gaseous constituent therethrough, and an auxiliary chamber is defined between the sample chamber and outside environment to limit the diffusion rate out of the sample chamber to an acceptable level.

In carrying out the above object and other objects and features of the present invention, a sample bag for collecting a sample of gaseous constituents is provided. The sample bag comprises an inner bag and an outer bag. The inner bag defines a sample chamber and has a wall that bounds the sample chamber. The wall is made of a material that allows limited diffusion through the wall of at least one of the gaseous constituents. The outer bag defines an auxiliary chamber at least partially bound by the wall such that limited diffusion between the sample chamber and the auxiliary chamber is allowed through the wall.

It is appreciated that the limited diffusion through the sample chamber wall is not a desirable result, but is a consequence for certain materials that may be selected for the wall. The present invention provides various configurations for a sample bag that substantially reduce any undesirable diffusion through the wall that may occur due to the selected material. Further, it is appreciated that it is not desirable to have a large number of diffusing constituents. But again, the present invention provides various configurations for a sample bag that substantially reduce any undesirable diffusion.

In one embodiment, the wall material is polytetrafluoroethylene (PTFE). Of course, the list of films that may be used in the alternative to PTFE is almost endless. In a preferred embodiment, the outer bag substantially encloses the inner bag such that the auxiliary chamber substantially surrounds the sample chamber. More preferably, the inner bag wall generally bounds the auxiliary chamber with respect to the sample chamber, and the outer bag is generally surrounded by an outside environment. Preferably, the outer bag includes an outside wall that bounds the auxiliary chamber with respect to the outside environment. The outside wall of the outer bag may be made of a material that allows limited diffusion through the outside wall of at least one of the gaseous constituents, for example, the outside wall material may also be polytetrafluoroethylene (PTFE).

Preferably, a first inlet is provided for filling the inner bag, and a second inlet is provided for filling the outer bag. Advantageously, the inner and outer bags may be filled with the same sample material, with the inner bag holding the actual sample to be analyzed, while the same sample material in the outer bag limits diffusion out of the inner bag to an acceptable level even though constituents may diffuse to the outside environment from the outer bag.

In some embodiments, the sample bag further comprises an additional bag defining an additional chamber. The outer bag has an outside wall that bounds the auxiliary chamber and the additional chamber is at least partially bound by the outer bag outside wall such that diffusion between the auxiliary chamber and the additional chamber takes place through the wall.

Further, in carrying out the present invention, a sample bag for collecting a sample of gaseous constituents comprises a plurality of barriers defining a plurality of nested chambers. The plurality of barriers defines the plurality of nested chambers and associated boundaries, including a sample chamber. A sample chamber boundary separates the sample chamber from at least one different chamber and is made of a material that allows limited diffusion through the sample chamber boundary of at least one of the gaseous constituents. The at least one different chamber has an outside wall that bounds the at least one different chamber with respect to an outside environment.

In a preferred implementation, the outside wall is made of a material that allows limited diffusion through the outside wall of at least one of the gaseous constituents such that diffusion from the sample chamber to the outside environment passes through the at least one different chamber. For example, the at least one of the barriers may be made of polytetrafluoroethylene (PTFE). The plurality of nested chambers may define an inner bag containing the sample chamber and an outer bag containing the at least one different chamber, or may define any other suitable group of nested chambers such that diffusion out of the actual sample chamber is limited to an acceptable level to preserve the integrity of the sample.

Still further, in carrying out the present invention, a method for collecting a sample of gaseous constituents from a source is provided. The method comprises collecting the sample in an inner bag, and collecting a control gas in an outer bag. The inner bag defines a sample chamber and has a wall that bounds the sample chamber. The wall is made of material that allows limited diffusion through the wall of at least one of the gaseous constituents in the sample. The outer bag defines an auxiliary chamber at least partially bound by the wall such that diffusion between the sample chamber and the auxiliary chamber takes place through the wall. The outer bag has an outside wall that bounds the auxiliary chamber with respect to an outside environment. The outer bag outside wall is made of material that allows limited diffusion through the outer bag outside wall of at least one of the gaseous constituents.

It is appreciated that embodiments of the present invention use a material to provide a barrier around the sample chamber wherein the material allows limited diffusion through the barrier of a gaseous constituent causing the relative concentrations of the constituents to vary. To preserve the integrity of the sample within the sample chamber, any number of additional chambers are defined about the sample chamber. These additional chambers are filled with a control gas, which may be the same gaseous mixture being sampled in the sample chamber. The gaseous constituent diffuses out of the one or more auxiliary chambers to the outside environment, as the same gaseous constituent diffuses from the sample chamber to the auxiliary chamber or chambers. Because the gaseous constituent content in the sample chamber and in the auxiliary chamber are relatively similar concentrations, diffusion out of the sample chamber is slow, preserving the integrity of the sample.

Of course, the inner bag wall and the outer bag outside wall may be made of essentially the same material having the same essential properties, or may be made of different materials. Further, the control gas for the outer bag need not be from the same source as the sample for the inner bag, and may be from a different source so long as the gaseous constituent content for the constituent that diffusion is to be controlled is sufficiently close to the content in the inner bag.

Even further, in carrying out the present invention, a sample bag for collecting a sample of gaseous mixture for emissions testing is provided. The mixture is a mixture of exhaust gasses and a dilution gas. The sample bag comprises an inner bag defining a sample chamber having an outer wall that bounds the sample chamber. The outer wall is made of material that allows limited diffusion through the outer wall of exhaust gasses. The sample bag further comprises an outer bag substantially enclosing the inner bag and defining an auxiliary chamber at least partially bound by the inner bag outside wall. Diffusion between the sample chamber and the auxiliary chamber is allowed through the inner bag outside wall. The outer bag has an outer bag outside wall made of material that allows limited diffusion through the outer bag outside wall of exhaust gasses to an external environment.

The above object, and other objects, features, and advantages of the present invention are readily apparent from the following detailed description of the best mode for carrying out the invention when taken in connection with the accompanying drawings.

BEST MODE FOR CARRYING OUT THE INVENTION

Figure 1:
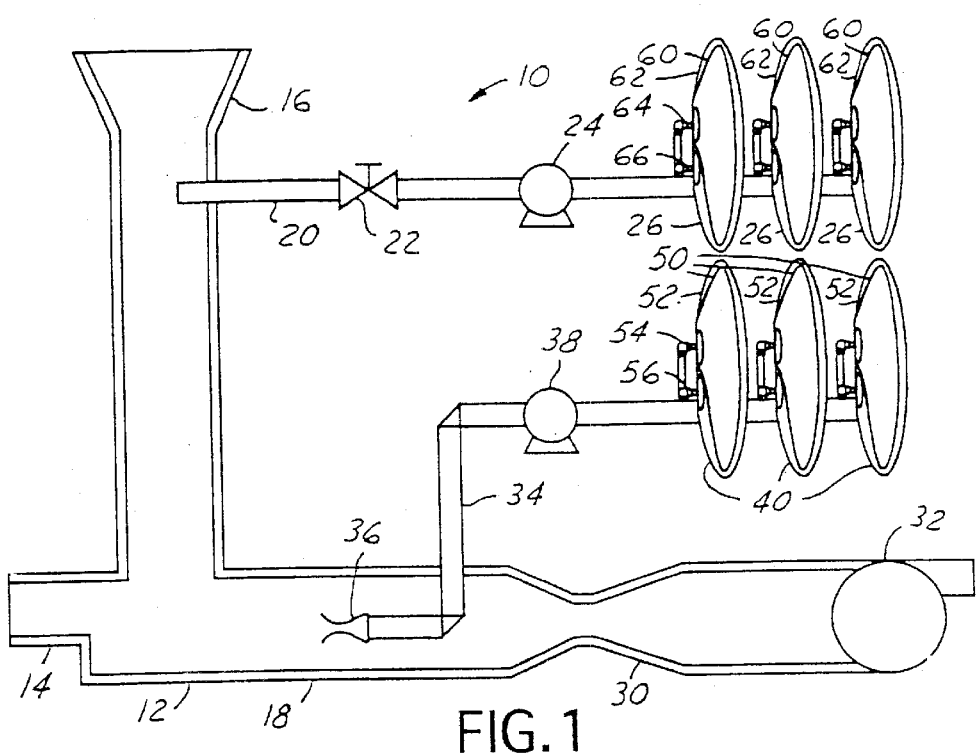
FIG. 1 is a mixing system connected to a plurality of sample bags that are made in accordance with the present invention.

With reference to FIG. 1, a mixing system of the present invention is generally indicated at 10. A gaseous inlet 14 receives the gasses to be tested such as, for example, a mixture of vehicle exhaust gasses. A dilution inlet 16 receives dilution gas which is typically air at ambient pressure, but may be a different gas at a different pressure. Filters (not shown) may be located at dilution inlet 16 to filter dust and dirt from the dilution gas, and are preferably used when the dilution gas is air. The dilution gas and the exhaust gasses come together at mixing portion 12. Of course, it is appreciated that although preferred embodiments of the present invention are suitable for collecting mixtures of exhaust gasses and dilution gas, embodiments of the present invention are suitable for the testing of other gasses, mixed or unmixed, and in other areas than emission testing.

A dilution gas sample line 20 draws a sample of the dilution gas. As mentioned previously, many times it is desirable to analyze the dilution gas, and analyze the gaseous mixture (dilution gas combined with exhaust gasses) to improve the accuracy of the end results of testing. Needle valve 22 maintains a nominally constant flow rate for the dilution gas sample through line 20, with the dilution gas being collected through pump 24 into sample bags 26.

During testing, raw exhaust from the vehicle under test enters gaseous inlet 14 and is mixed with dilution gas at mixing portion 12. The mixture of dilution gas and exhaust gasses passes from mixing portion 12 to mixture outlet 18. The mixed gasses are drawn through a main venturi 30 by a blower 32. Main venturi 30 is choked and meters and measures the flow of the combined gasses. A mixture sample line 34 connects to mixture outlet 18 through a smaller, sample venturi 36 also operated in choked condition. A pump 38 cooperates with sample venturi 36 to fill sample bags 40 of the present invention with the mixed gasses for later analysis.

When air is used as the dilution gas, there are measurable amounts of pollutants in the dilutant gas. Typically, the pollutant concentration in the dilution sample bags 26 and in the mixture sample bags 40 are used together to determine emission content using techniques that are known in the art. Embodiments of the present invention provide new and improved sample bags that, for certain applications, increase the integrity of the collected samples.

In developing embodiments of the present invention, the inventor faced the problem of a polyvinylfloride (PVF) resin sample bag contributing hydrocarbons to the gas mixture sample inside the bag. To overcome the hydrocarbon problem of the PVF bag, the inventor tested a polytetrafluoroethylene (PTFE) sample bag. The PTFE bag overcomes the problem of hydrocarbon contribution from the bag walls, but allows limited diffusion of small but significant amounts of carbon dioxide through the PTFE bag wall. Embodiments of the present invention address the problem of carbon dioxide diffusing through the PTFE bag walls by providing nested chambers that limit the diffusion rate out of the sample chamber to an acceptable level. In a preferred embodiment in which the sample bag is used to collect diluted exhaust gas mixtures, the inventor has found that material sold under the name TEFLON is suitable.

It is appreciated that the limited diffusion through the sample chamber wall is not a desirable result, but is a consequence for certain materials that may be selected for the wall. The present invention provides various configurations for a sample bag that substantially reduce any undesirable diffusion through the wall that may occur due to the selected material. Further, it is appreciated that it is not desirable to have a large number of diffusing constituents. But again, the present invention provides various configurations for a sample bag that substantially reduce any undesirable diffusion.

Of course, it is appreciated that embodiments of the present invention may be used in a variety of applications in which a typical sample bag, due to the properties of the bag wall, has limited but significant diffusion occurring through the wall, and that a PTFE bag is just an example of a suitable bag material for the particular application of collecting a diluted exhaust gas mixture. Because the sample bag material in sample bags of the present invention does allow diffusion of a gas constituent in the sample chamber (carbon dioxide in the example), some of the diffusing component does pass from the sample chamber to the outer environment. However, the sample bag structure does limit the diffusion rate to an acceptable level that does not cause a significant change in the relative concentrations within the sample chamber. That is, a sample bag having a structure made in accordance with the present invention is designed to reduce the change in concentration of the diffusing component in the sample chamber to an acceptable level by employing nested chambers (with the inner and outer bag embodiment being one suitable implementation).

As shown in FIG. 1, the sample bags in the illustrated embodiments of the present invention that are used to collect mixture samples each include an inner bag 50 and an outer bag 52. Inner bag 50 receives gasses through inlet 54, while outer bag 52 receives gasses through inlet 56. The dilution gas sample bags 26, in the illustrated embodiment, each include an inner bag 60 and an outer bag 62. Inner bag 60 receives gasses through inlet 64, while outer bag 62 receives gasses through inlet 66.

Figure 2:
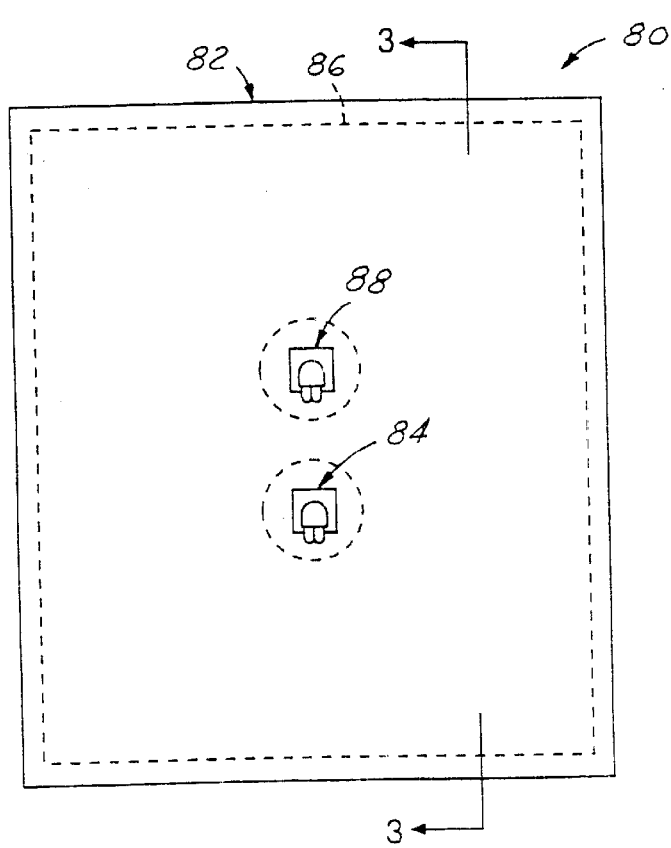
FIG. 2 is a front view of a sample bag of the present invention.
Figure 3:
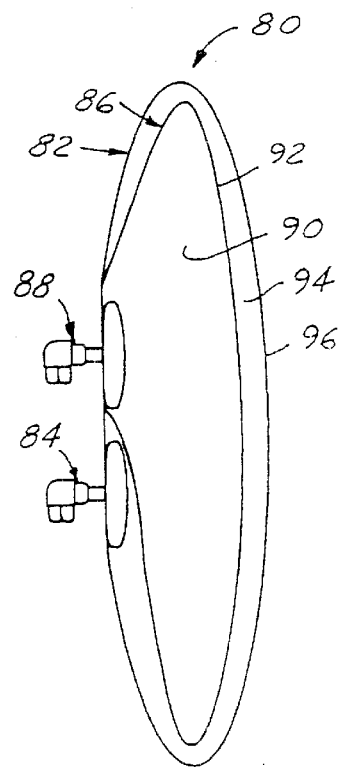
FIG. 3 is a cross sectional view of the sample bag taken along line 3—3 of FIG. 2.

With reference to FIGS. 2 and 3, a sample bag in a preferred embodiment of the present invention is generally indicated at 80. Sample bag 80 is made up of an outer bag 82 that receives gasses through inlet 84, and an inner bag 86 that receives gasses through inlet 88. Inner bag 86 defines a sample chamber 90. Chamber 90 is enclosed by a wall 92 that bounds the sample chamber. Wall 92 is made of a material that allows limited diffusion through the wall of at least one of the gaseous constituents of the sample gas. To slow the diffusion of the diffusing gaseous constituent that is exiting sample chamber 90 through chamber wall 92, outer bag 82 is filled with a control gas. Outer bag 82 defines an auxiliary chamber 94. Auxiliary chamber 94 is bound by wall 96. The control gas within outer bag 82 has a concentration of the diffusing constituent gas that approximates the concentration of the diffusing constituent within the sample chamber. By keeping the concentration of the diffusing gas approximately equal in the sample and auxiliary chambers, the diffusion through wall 92 is slowed to an acceptable rate. That is net diffusion out of the sample chamber is limited.

One way to cause the concentrations of the diffusing gas to be close to each other is to fill both the inner bag and the outer bag with the gas being sampled. Only the gas from the sample chamber is later analyzed. However, keeping that same gas in the outer bag reduces the amount of net diffusion through wall 92 that, without the outer bag, would diffuse into the external environment. That is, because the concentration of the constituent to be measured in the external environment is most likely much different than the concentration within the sample chamber of that same component, direct interfacing of wall 92 with the external environment would result in significant diffusion of the constituent out of the sample chamber 90. Advantageously, embodiments of the present invention provide an auxiliary chamber adjacent to the parts of the sample chamber wall made of a material that allows diffusion, and the auxiliary chamber is filled with a gas having a concentration such that net diffusion is substantially reduced.

It is appreciated that embodiments of the present invention are not limited to the particular preferred sample bag shown in FIGS. 2 and 3. The present invention is a sample bag in which at least part (and in the embodiment illustrated, all) of the sample chamber is bound by a wall made of a material that allows limited diffusion through the wall of a gaseous constituent. In accordance with the present invention, to reduce the effects of this diffusion on the relative concentrations of that constituents within the sample chamber, an auxiliary chamber is defined such that diffusing gasses passing through the wall of the sample chamber enter into the auxiliary chamber. The auxiliary chamber, in accordance with the present invention is filled with a gas that has a gaseous constituent content for the diffusing gasses that approximates the concentration within the sample chamber such that net diffusion is reduced to an acceptable level. A suitable material for chamber walls that allow limited diffusion is polytetrafluoroethylene (PTFE). Of course, depending on the particular constituents in the sample chamber, the appropriate material for the wall may vary.

Depending on the constituents in the sample, the wall may be made of any commonly known film, such as the proprietary materials of TEFLON, TEDLAR, or SARAN, in addition to other materials such as polyvinylchloride (PVC), polyethylene, polypropylene, polyester (PET), cellulose acetate, polystyrene, etc., in addition to PTFE. Further, as the sample bag may be made with nested chambers in a variety of ways, some of the films may include a variety of metal films plated on them. Of course, the selection of a wall material should be made with consideration being given to the gasses being sampled. For example, when sampling a diluted exhaust gasses mixture, TEFLON is a suitable material.

It is appreciated that the limited diffusion through the sample chamber wall is not a desirable result, but is a consequence for certain materials that may be selected for the wall. The present invention provides various configurations for a sample bag that substantially reduce any undesirable diffusion through the wall that may occur due to the selected material. Further, it is appreciated that it is not desirable to have a large number of diffusing constituents. But again, the present invention provides various configurations for a sample bag that substantially reduce any undesirable diffusion.

That is, the embodiments of the present invention include multiple layers of the same film or combinations of various types of films. In one example, the sample bags shown in FIGS. 2 and 3 could be supplemented with additional auxiliary chambers surrounding the outer bag. That is, the inner bag may be surrounded by an outer bag, surrounded by another outer bag, and so on. Further, in another example, the inner bag may be surrounded by one outer bag about one portion of the inner bag, and by another outer bag along another portion of the inner bag. In accordance with the present invention, a plurality of barriers of the same material or film or different materials of films define a plurality of nested chambers and associated boundaries. A sample chamber, such as the inner bag in the exemplary embodiments has a boundary that is made of a material that allows the limited diffusion through the sample chamber boundary of a gaseous constituent in the sample. The auxiliary chamber or arrangement of chambers are filled with appropriate gas or gas mixture to control and limit diffusion out of the sample chamber.

Figure 4:
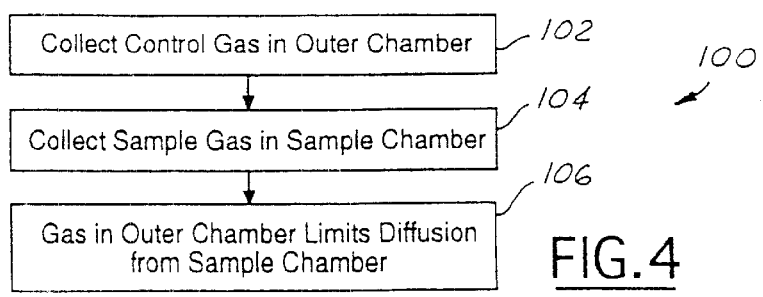
FIG. 4 is a block diagram illustrating a method of the present invention for collecting a gas sample.

With reference to FIG. 4, a method of the present invention is depicted in a block diagram, generally indicated at 100. At block 102, control gas is collected in an outer chamber, such as the outer bag 82 (FIGS. 2 and 3). At block 104, a sample gas is collected in the sample chamber, such as an inner bag 86 (FIGS. 2 and 3). At block 106, gas in the outer chamber limits the net diffusion from the sample chamber of a constituent to preserve the integrity of relative concentrations in the sample.

Figure 5:
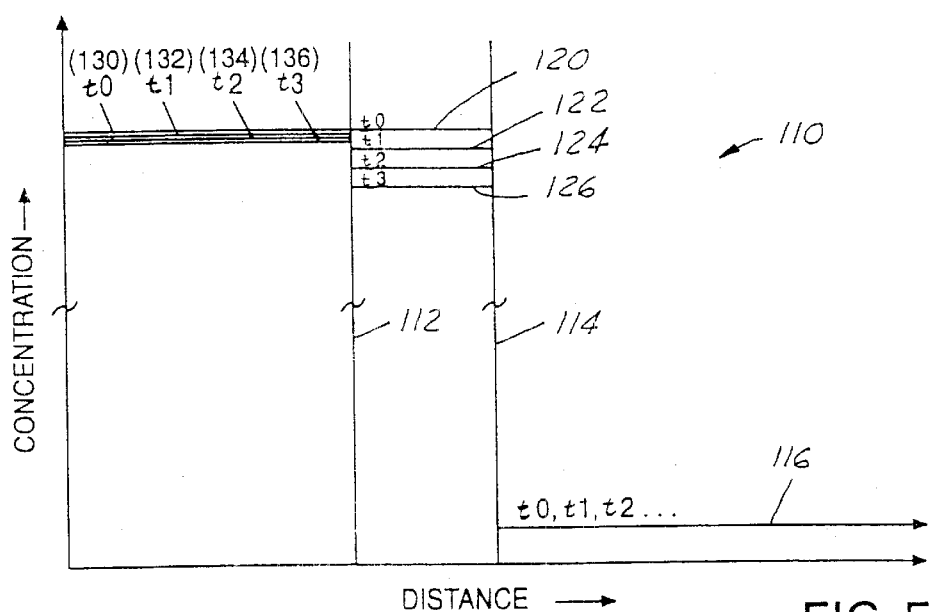
FIG. 5 is a graph depicting a collection of level curves, illustrating concentration levels in the sample chamber, auxiliary chamber, and outside environment, at different times.

With reference to FIG. 5, a plurality of level curves, generally indicated at 110, illustrate concentration versus location. Concentration is indicated by the ordinate, with distance indicated by the abscissa. The distance is indicated with the origin being the center of the sample chamber, and as distance increases, location passes through an auxiliary chamber, and then to the external environment. The sample chamber boundary is indicated at 112, with the outer most boundary of the sample bag being indicated at 114. FIG. 5 illustrates concentrations for the inner and outer bag embodiment, shown in FIGS. 2 and 3. Level curve 116 represents concentration of the constituent in the external environment. Generally, concentration of the constituent in the external environment may be approximated as constant. In the illustration in FIG. 5, both the inner bag and the outer bag are originally (at time t0) filled with the sample gas. Level curves 120, 122, 124, 126 illustrate the changing of the concentration of the constituent within the outer bag over time (with curves being shown for t=t0, t1, t2, t3, respectively). That is, the constituent diffuses through barrier 114, and the rate of diffusion with respect to time is related to the difference in concentrations between the outer bag and the external environment.

Concentrations of the constituent within the sample chamber, over time, are indicated by level curves 130, 132, 134, 136 (for t=t0, t1, t2, t3, respectively. The level curves 130, 132, 134, 136 indicate the concentration within the sample chamber (inner bag) as the constituent diffuses through wall or barrier 112 of the sample chamber. As illustrated, the rate of diffusion of the constituent from the inner bag, through wall 112, to the outer bag is related to the difference in concentrations of the constituent in the adjacent chambers. Embodiments of the present invention are configured such that the difference in concentrations across inner bag outside wall 112, is reduced to slow the diffusion across wall 112. As shown, the advantages of using the auxiliary chamber are readily apparent by comparing the change in concentration levels over time of the outer bag to the change in concentration levels over time to the inner bag. Clearly, the concentration levels within the inner bag are preserved to a greater degree than those in the outer bag, in accordance with the present invention.

Figure 6:
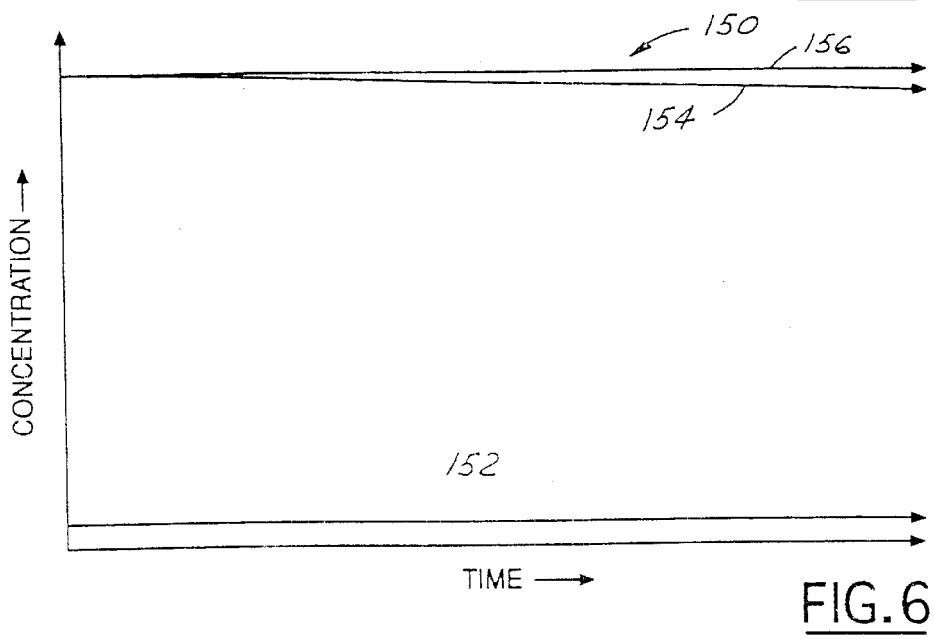
FIG. 6 is a graph depicting concentration versus time for the sample chamber, auxiliary chamber, and outside environment, in accordance with the level curves depicted in FIG. 5.

As best shown in FIG. 6, several concentration versus time curves are generally indicated at 150. Curve 152 illustrates concentration versus time in the external environment (corresponds to level curve 116). Curve 154 illustrates concentration versus time in the outer bag (corresponds to level curves 120, 122,124, 126). And, curve 156 illustrates concentration versus time in the inner bag (corresponds to level curves 130, 132, 134, 136).

Of course, it is appreciated that the information shown in the graphs of FIGS. 5 and 6 is meant to illustrate the effects of the sample bag of the present invention on concentration levels in various chambers of the bag, with the graph showing concentrations in the exemplary two chamber embodiment. As such, it is appreciated that actual concentration curves may vary significantly, depending on many factors, as is appreciated by those skilled in the art. For example, it is well known by those skilled in the art that many factors affect diffusion rate such as, for example, the barrier material and temperature, to name two. Further, it is appreciated that the illustrated graphs are not necessarily to an exact scale, and that actual concentration curves may vary significantly.

For example, one way to describe the diffusion process, that is appreciated by those skilled in the art, is using Fick's laws. Fick's first law uses a diffusion coefficient to relate the component flux to a position derivative of component distribution, and Fick's second law relates a time derivative of component distribution to the divergence of the component flux. Both Fick's first and second laws may be combined to analyze various different cases of diffusion, as is appreciated by those skilled in the art of gaseous constituent measuring.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for collecting a sample of gaseous constituents from a source of exhaust gases, the method comprising:

collecting the sample in an inner bag defining a sample chamber and having a wall that bounds the sample chamber, the wall being made of a material that allows limited diffusion through the wall of at least one of the gaseous constituents in the sample; and collecting a control gas in an outer bag defining an auxiliary chamber at least partially bound by the wall such that diffusion between the sample chamber and the auxiliary chamber takes place through the wall, the outer bag having an outside wall that bounds the auxiliary chamber with respect to an outside environment and that is made of a material that allows limited diffusion through the outer bag outside wall of the at least one of the gaseous constituents, wherein said control gas controls the rate of diffusion of said at least one gaseous constituent through said wall.

2. The method of claim 1 wherein the inner bag wall and the outer bag outside wall are made of essentially the same material.

3. The method of claim 1 wherein collecting the control gas further comprises:

collecting the control gas for the outer bag from the same source as the sample for the inner bag.

4. The method of claim 1 wherein collecting the control gas further comprises:

collecting the control gas for the outer bag from a different source as the sample for the inner bag.

* * * * *